US 10,716,543 B2

United States Patent
Haugaard et al.

(10) Patent No.: US 10,716,543 B2
(45) Date of Patent: Jul. 21, 2020

(54) ULTRASOUND VECTOR FLOW IMAGING (VFI) WITH CURVE TRACING

(71) Applicant: B-K MEDICAL APS, Herlev (DK)

(72) Inventors: Per Haugaard, Skovlunde (DK); Gert Seerup, Hilleroed (DK)

(73) Assignee: B-K Medical ApS, Herlev (DK)

( * ) Notice: Subject to any disclaimer, the term of this patent is extended or adjusted under 35 U.S.C. 154(b) by 738 days.

(21) Appl. No.: 14/775,178

(22) PCT Filed: Mar. 13, 2013

(86) PCT No.: PCT/IB2013/000379
§ 371 (c)(1),
(2) Date: Sep. 11, 2015

(87) PCT Pub. No.: WO2014/140657
PCT Pub. Date: Sep. 18, 2014

(65) Prior Publication Data
US 2016/0015366 A1      Jan. 21, 2016

(51) Int. Cl.
*A61B 8/08* (2006.01)
*A61B 8/00* (2006.01)
(Continued)

(52) U.S. Cl.
CPC .............. *A61B 8/5223* (2013.01); *A61B 8/06* (2013.01); *A61B 8/065* (2013.01); *A61B 8/145* (2013.01);
(Continued)

(58) Field of Classification Search
None
See application file for complete search history.

(56) References Cited

U.S. PATENT DOCUMENTS 5,390,677 A * 2/1995 Ferrera ................ A61B 8/06
600/455
5,409,010 A * 4/1995 Beach ................. A61B 8/06
600/455

(Continued)

FOREIGN PATENT DOCUMENTS

WO       2001097704 A2    12/2001

OTHER PUBLICATIONS

Uejima et al., "A new echocardiographic method for identifying vortex flow in the left ventricle: numerical validation". Ultrasound in Med. & Biol., 2010 vol. 36, No. 5, pp. 772-778.*
(Continued)

*Primary Examiner* — Katherine L Fernandez
*Assistant Examiner* — Yi-Shan Yang
(74) *Attorney, Agent, or Firm* — Anthony M. Del Zoppo, III; Daugherty & Del Zoppo Co., LPA

(57) ABSTRACT

An ultrasound imaging system (100) includes a velocity processor (118) that processes ultrasound data representing structure flowing through a tubular object and generates vector flow imaging information indicative of the structure flowing through a tubular object based thereon. The vector flow imaging information includes an axial velocity component signal and a lateral component signal, and the axial and lateral component signals indicate a direction and a speed of the structure flowing through the tubular object. The ultrasound imaging system further includes a flow parameter processor (120) that determines at least one flow parameter based on the vector flow imaging information and generates a signal indicative thereof.

24 Claims, 5 Drawing Sheets

(51) Int. Cl.
*A61B 8/06* (2006.01)
*A61B 8/14* (2006.01)
*G01S 15/89* (2006.01)

(52) U.S. Cl.
CPC ............ *A61B 8/4483* (2013.01); *A61B 8/463* (2013.01); *A61B 8/469* (2013.01); *A61B 8/5207* (2013.01); *A61B 8/0891* (2013.01); *G01S 15/8984* (2013.01)

(56) References Cited

U.S. PATENT DOCUMENTS

| | | | | |
|---|---|---|---|---|
| 6,148,224 | A * | 11/2000 | Jensen | G01P 3/64 |
| | | | | 324/306 |
| 6,464,641 | B1 * | 10/2002 | Pan | A61B 8/06 |
| | | | | 600/453 |
| 2007/0016046 | A1 * | 1/2007 | Mozayeni | A61B 8/06 |
| | | | | 600/443 |
| 2007/0016050 | A1 * | 1/2007 | Moehring | A61B 8/06 |
| | | | | 600/454 |
| 2007/0258632 | A1 * | 11/2007 | Friedman | A61B 8/08 |
| | | | | 382/128 |
| 2008/0269611 | A1 * | 10/2008 | Pedrizzetti | A61B 8/06 |
| | | | | 600/454 |
| 2011/0196237 | A1 * | 8/2011 | Pelissier | A61B 8/06 |
| | | | | 600/454 |
| 2014/0371594 | A1 * | 12/2014 | Flynn | G01S 15/8984 |
| | | | | 600/454 |

OTHER PUBLICATIONS

Ohtsuki et al., "The flow velocity distribution from the Doppler information on a plane in three-dimensional flow". Journal of Visualization, vol. 9, No. 1, 2006, pp. 69-82.*

Sengupta et al., "Emerging trends in CV flow visualization". JACC, 2012, vol. 5, No. 3, pp. 305-316.*

International search report for PCT/IB2013/000379 published as WO 2014/140657.

* cited by examiner

ULTRASOUND VECTOR FLOW IMAGING (VFI) WITH CURVE TRACING

RELATED APPLICATION

This application is a national filing of PCT application Serial No. PCT/IB2013/000379, filed Mar. 13, 2013, published as WO2014/140657 on Sep. 18, 2014. This application claims priority to PCT application Serial No. PCT/IB2013/000379, published as WO2014/140657 on Sep. 18, 2014.

TECHNICAL FIELD

The following generally relates to ultrasound imaging and more particularly to ultrasound velocity flow imaging (VFI) with curve tracing.

BACKGROUND

Color flow mapping (CFM) is one approach to estimate and visualize the flow inside blood vessels in a combined B and CFM duplex mode. Either the CFM image covers the complete field of view equal to the B-mode image or the user places a box using the graphical user interface (GUI) of the ultrasound system to indicate a region of interest (ROI). Unfortunately, CFM only shows relative blood flow information of whether the flow is towards or away from the transducer. Hence, it cannot show absolute flow direction or absolute velocities.

For quantitative information about blood flow, spectral Doppler (D) imaging has been used with B mode and CFM imaging. Generally, spectral Doppler imaging displays information about the power spectral density of the received blood flow Doppler-shift frequencies in the form of a real-time updating of a 2D spectrogram image. The display simultaneously displays a B-mode image and a D-mode information along with the spectrogram. The spectrogram has been defined by Doppler frequency-shift along the y-axis and time along the x-axis. The intensity of each pixel in the spectrogram represents the signal power and the value range has been indicated by a color or gray-scale bar.

Spectral Doppler imaging with automatic velocity curve tracing has been used to measure a mean velocity and a maximum velocity as a function of time. Generally, automatic velocity curve tracing automatically measures these parameters and plots the measurements via curves on the display, e.g., overlaid on top of the spectrogram. Information such as the nature of the blood flow (e.g., its complexity, level of retrograde-flow, level of turbulence, etc.) can be indirectly obtained through recognizing the look of the spectrogram and the sound of the Doppler audio produced by the scanner. The user may also measure the volume flow through the vessel.

By way of example, the user first scans the blood vessel of interest with the probe in B mode and CFM mode. Next, the user activates D mode with automatic velocity curve tracing. The user then places the Doppler gate at the blood vessel. While positioning the probe to get a scan-plan through the blood vessel of interest, the user places an axial scan-line with a Doppler gate across the vessel. The spectrogram is then formed from data received from this Doppler-gate. To get velocity information along the y-axis in the spectrogram instead of Doppler-shift frequency, the user has to set a beam-to-flow angle by indicating the general direction of the blood vessel and flow.

This angle has been less than or equal to sixty degrees (60°) for acceptable precision in the resulting velocity estimations. The user then adjusts the Doppler gate size to cover a cross-section of the vessel. The user then steadies the probe and acquires data for at least two heart beats. The user then freezes or pauses scanning and activates volume flow estimates. The user then manually measure the cross-section or diameter of the vessel on the B-mode image where the Doppler gate is located, and the system calculates an estimate of the volume flow based on the mean velocity curve trace for a user selected section and of the spectrogram and shows the result in a measurement area.

Unfortunately, the above process concurrently using B mode, CFM mode and D mode imaging can be complex and tedious.

SUMMARY

Aspects of the application address the above matters, and others.

In one aspect, an ultrasound imaging system includes a velocity processor that processes ultrasound data representing structure flowing through a tubular object and generates vector flow imaging information indicative of the structure flowing through a tubular object based thereon. The vector flow imaging information includes an axial velocity component signal and a lateral component signal, and the axial and lateral component signals indicate a direction and a speed of the structure flowing through the tubular object. The ultrasound imaging system further includes a flow parameter processor that determines at least one flow parameter based on the vector flow imaging information and generates a signal indicative thereof.

In another aspect, a method includes processing ultrasound data representing structure flowing through a tubular object and generating vector flow imaging information indicative of the structure flowing through a tubular object based thereon. The vector flow imaging information includes an axial velocity component signal and a lateral component signal, and the axial and lateral component signals indicate a direction and a speed of the structure flowing through the tubular object. The method further includes determining at least one flow parameter based on the vector flow imaging information and generating a signal indicative thereof.

In another aspect, a computer readable storage medium is encoded with computer readable instructions. The computer readable instructions, when executed by a processor, causes the processor to: process ultrasound data representing structure flowing through a tubular object and generating vector flow imaging information indicative of the structure flowing through a tubular object based thereon. The vector flow imaging information includes an axial velocity component signal and a lateral component signal, and the axial and lateral component signals indicate a direction and a speed of the structure flowing through the tubular object. The computer readable instructions, when executed by a processor, further causes the processor to: determine at least one flow parameter based on the vector flow imaging information and generating a signal indicative thereof.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

The following describes an approach for ultrasound VFI imaging with automatic curve tracing. In one instance, this approach provides direct visualization of the general nature of the blood flow and automatically calculates velocity and/or volume flow curve trace information, which mitigates using spectral Doppler to determine such information, which can simplify user interaction with the scanner.

Figure 1:
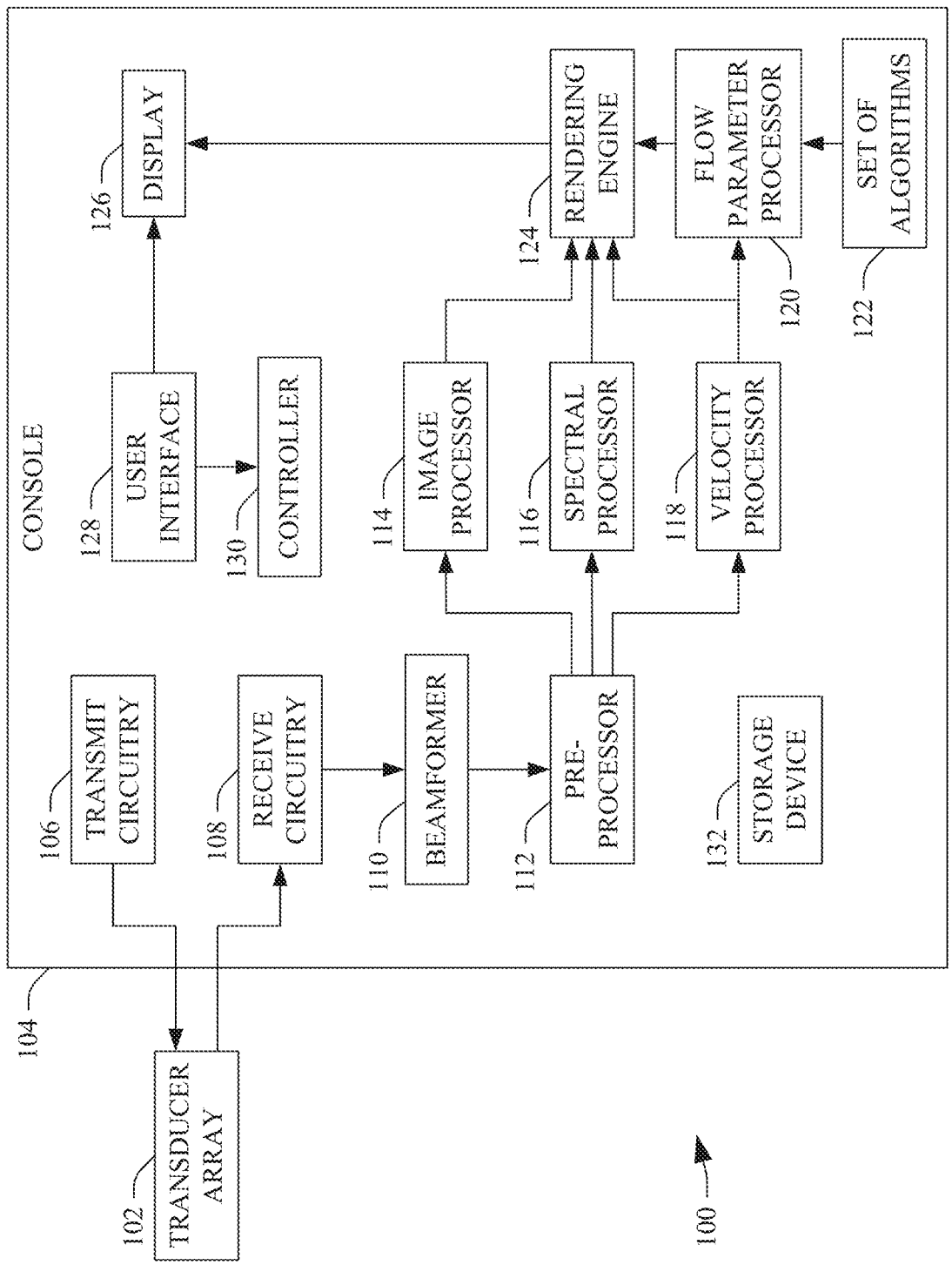
FIG. 1 schematically illustrates an example ultrasound imaging system including a velocity processor and a flow parameter processor.

FIG. 1 schematically illustrates an example ultrasound imaging system 100. The system 100 includes a transducer array 102 that interfaces with a console 104 via a suitable wire and/or wireless interface.

The transducer array 102 converts an electrical signal to an ultrasound pressured field and vice versa. More specifically, the transducer array 102 includes an array of one or more transducer elements that are configured to transmit ultrasound signals and receive echo signals. Examples of suitable arrays include 128, 192, and/or other elements arrays, including rectangular arrays. The array can be linear, curved, and/or otherwise shaped, fully populated, sparse and/or a combination thereof, etc.

The console 104 includes transmit circuitry 106 and receive circuitry 108.

The transmit circuitry 106 generates a set of pulses (or a pulsed signal) that are conveyed, via hardwire and/or wirelessly, to the transducer array 102. The set of pulses excites a set of the transducer elements of the transducer array 102, causing the excited transducer elements to transmit ultrasound signals into an examination or scan field of view. In one instance, the transmit ultrasound signals traverse structure flowing through a portion of a tubular structure in the scan field of view such as blood cells flowing through a portion of a blood vessel in the scan field of view.

The receive circuitry 108 receives a set of echoes (or echo signals) generated in response to the transmitted ultrasound signals, for example, in response to the ultrasounds field traversing structure such as blood flowing in a portion of a vessel and/or organ cells in a region of interest in the scan field of view and/or other structure.

Figure 2:
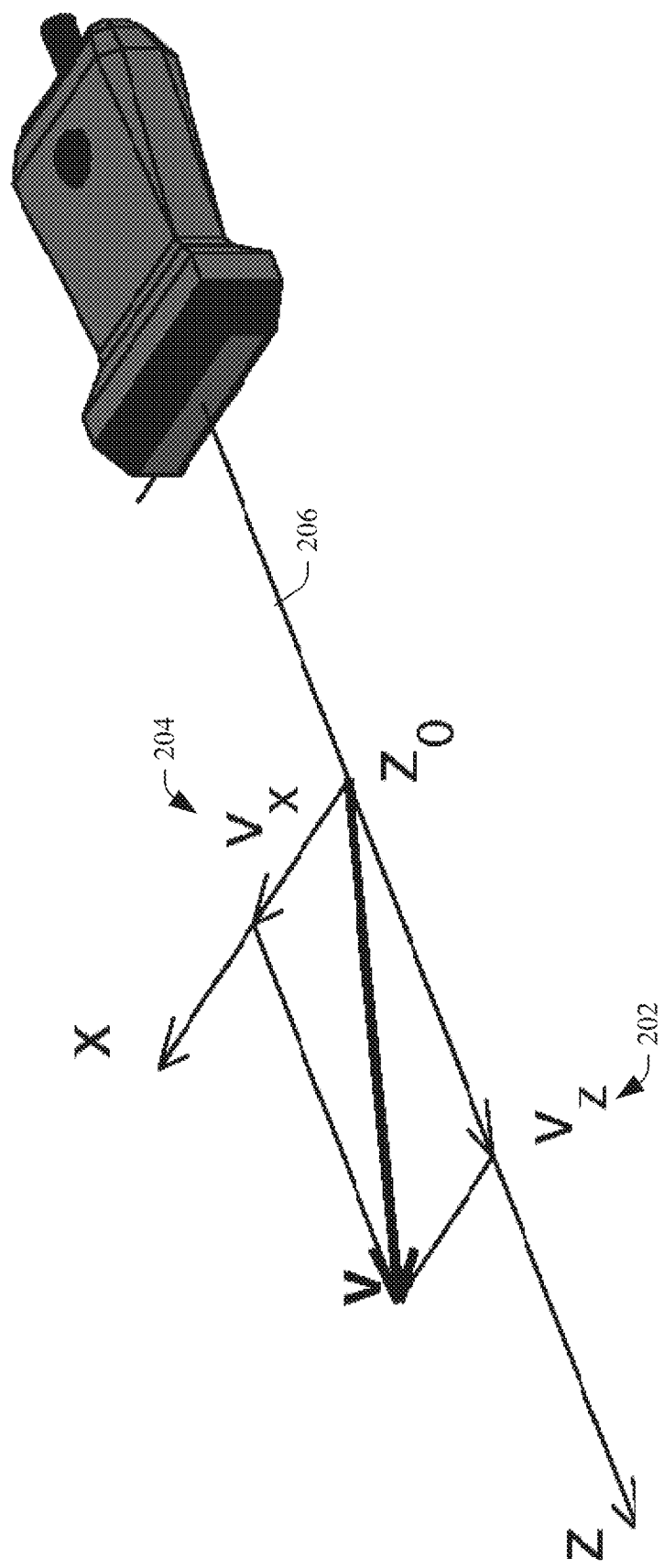
FIG. 2 illustrates axial velocity and lateral velocity components of a transmitted ultrasound signal.

The console 104 further includes a beamformer 110 that processes the echoes by applying time delays to echoes, weighting echoes, summing delayed and weighted echoes, and/or otherwise beamforming received echoes, creating a beam of RF data. For VFI, the beamformer 110 produces at least one beam to estimate an axial velocity component (Vz) 202, which extends along a direction 206 of a propagating beam, and at least two beams to estimate a lateral velocity component (Vx) 204, which extends transverse to the axial velocity component (Vz) 202, as shown in FIG. 2.

The console 104 further includes a pre-processor 112 that pre-processes the beamformed scan-lines. Suitable pre-processing includes, but is not limited to echo-cancellation, wall-filtering, basebanding, averaging and decimating, and/or other functions associated with VFI imaging and/or other imaging. The pre-processor 112 outputs pre-processed or ultrasound data. Two or more of the receive circuitry 108, the beamformer 110 or the pre-processor 112 can be considered as processing circuitry.

The console 104 further includes an image processor 114 that processes the pre-processed data. For B-mode imaging, this may include, e.g., envelope detection, log-compression, and/or other processing. The image processor 114 may also process scan-lines to lower speckle and/or improve specular reflector delineation, and/or perform other processing such as FIR and/or IIR filtering, etc.

The illustrated console 104 further includes an optional spectral processor 116 that also processes the pre-processed data, but generates spectral data such as a spectrogram and/or other spectral data. In a variation, the optional spectral processor 116 is omitted from the ultrasound imaging system 100.

A velocity processor 118 also processes the pre-processed data, generating vector flow imaging information. In one instance, this includes generating the axial and lateral velocity components. Generally, the axial and lateral velocity components indicate a direction and a speed of flowing structure in the field of view. An example of a suitable approach for determining the axial and the lateral velocity components based on autocorrelation is described in U.S. Pat. No. 6,859,659 B1, filed on Nov. 9, 2001, and entitled "Estimation of Vector Velocity," which is incorporated herein by reference in its entirety. Other approaches for determining the axial and lateral velocity components and/or a transverse component Vy, which is transverse to Vx and Vz, are also contemplated herein.

A flow parameter determiner 120 receives, as an input, the output of the velocity processor 118 and employs one or more flow parameter algorithms from a set of algorithms 122, which generate one or more flow parameters based on the input. In one instance, the one or more algorithms 122 include algorithms for determining one or more of an axial mean velocity, an axial maximum velocity, a mean velocity, a maximum velocity, mean volume flow, a time average mean velocity flow, a stroke volume, a velocity variance, a velocity standard deviation, peak systolic velocity, end diastolic velocity, a resistivity index, volume flow vessel cross-section area, and/or other flow and/or non-flow based information from the vector flow imaging information.

A rendering engine 124 visually presents, via a display 126 and/or other display, one or more the images (generated by the image processor 114), the vector flow information (generated by the velocity processor 118), and/or the one or more flow parameters (generated by the flow parameter processor 120). In one instance, the one or more flow parameters are visually presented as numerical values and/or graphically as a plot or curve, which are updated in real-time, or as data is being acquired by the transducer array 102 and processed through the beamformer 110, the pre-processor 112, the velocity processor 118 and the flow parameter processor 120.

Figure 3:
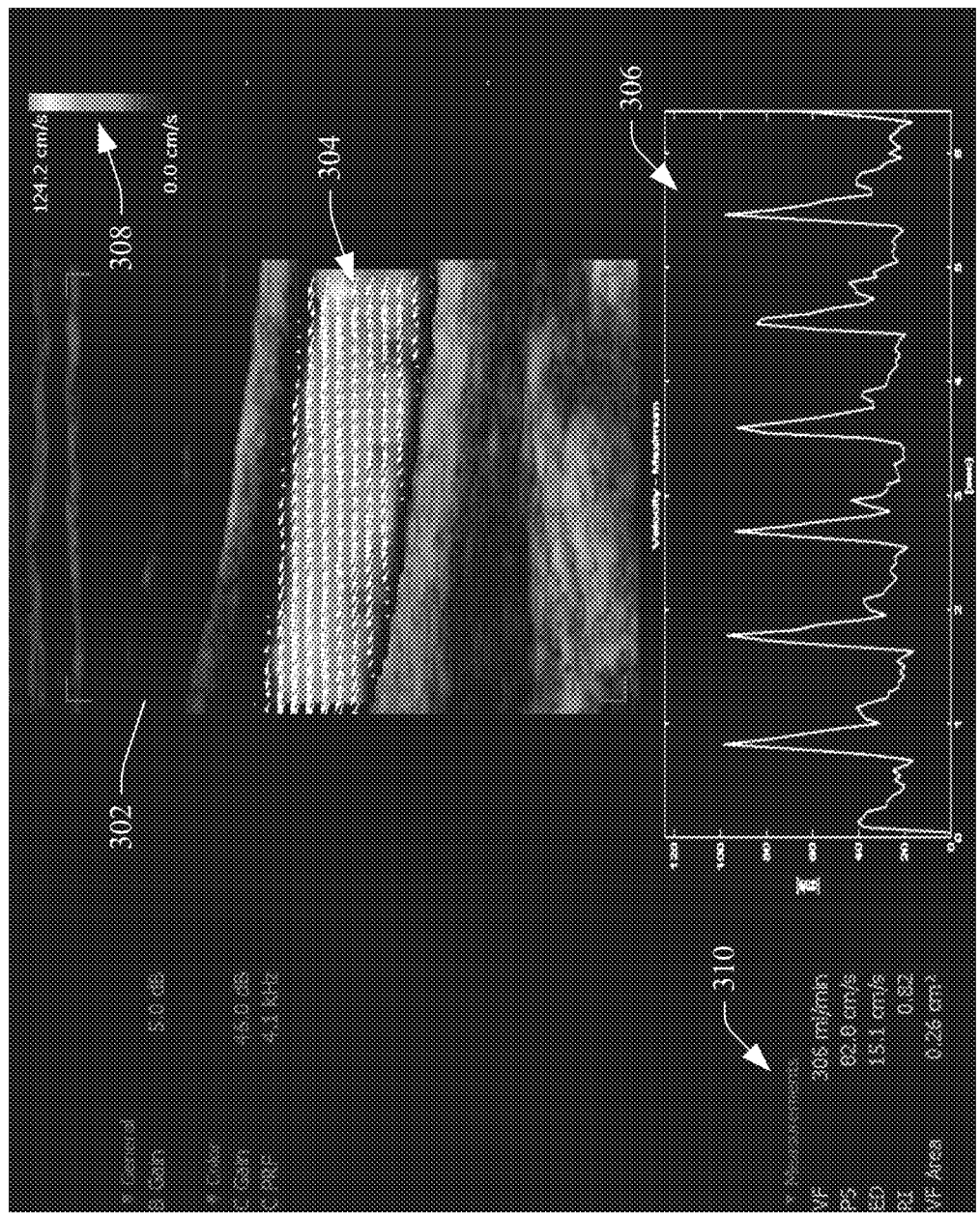
FIG. 3 illustrates a graphical user interface displaying at least a B mode image, vector flow imaging information superimposed there over, and a graphical plot of at least one determined flow parameter versus time.

By way of non-limiting example, FIG. 3 concurrently shows a B mode image 302, vector flow imaging information 304 superimposed over the B mode image 302, and a curve trace 306 illustrating maximum velocity as a function of time. In FIG. 3, the vector flow imaging information 304 is displayed in gray levels representing flow magnitude with arrow indicia superimposed there over indicating direction. A gray scale bar 308 maps the gray levels to a predetermined flow range. Other indicia such as color, arrow length, and/or other indicia can additionally or alternatively be used to show magnitude and/or direction. FIG. 3 also visually presents numerical information 310 such as volume flow, peak systolic velocity, end diastolic velocity, a resistivity index, and volume flow vessel cross-section area.

The velocity processor 118 can process the ultrasound data as the ultrasound data is produced, the flow parameter processor 120 can process the velocity flow imaging information as the velocity flow imaging information is produced, and the rendering engine can visually display the velocity flow imaging information and the at least one flow parameter as the velocity flow imaging information and the at least one flow parameter are produced. As such, the velocity flow imaging information and the at least one flow parameter can be updated in real time. Additionally, the image processor 114 can process the ultrasound data as the ultrasound data is produced, and, as such, the one or more images can be updated in real time.

Returning to FIG. 1, the rendering engine 124 can also visually display at least one of a velocity or a volume flow profile curve as a function of time versus at least one of an axial or a lateral distance through the tubular structure. The rendering engine 124 can also visually display at least one of a velocity or a volume flow profile curve as a function of time versus a spatial line through the tubular structure. In one instance, the visually displayed at least one flow parameter indicates a direction of flow within the tubular structure. In addition, the visually displayed at least one flow parameter indicates a cross-section area of the tubular structure. Furthermore, at least one flow parameter can be determined for a predetermined region of interest, which is a sub-region of the tubular structure, or the entire tubular structure.

A user interface (UI) 128 include one or more input devices (e.g., a button, a knob, a slider, a touch pad, a mouse, a trackball, a touch screen, etc.) and/or one or more output devices (e.g., a display screen, a light, an audio generator, etc.), which allow for interaction between a user and the ultrasound imaging system 100.

A controller 130 controls one or more of the components of the console 104. Such control can be based on a mode of operation (e.g., B mode and VFI mode with automatic curve trace, etc.) and/or otherwise.

A storage device 132 can be used to store one or more of the received set of echoes and/or data output by one or more of beamformer 110, the pre-processor 112, the image processor 114, the spectral processor 116, the velocity processor 118, the flow parameter processor 120 or the rendering engine 124. One or more of the received set of echoes and/or the data output by one or more of beamformer 110, the pre-processor 112, the image processor 114, the spectral processor 116, the velocity processor 118, the flow parameter processor 120 or the rendering engine 124 can also be stored on a portable memory device, conveyed over a network, filmed, printed, and/or otherwise utilized.

It is to be appreciated that one or more of the component beamformer 110, the pre-processor 112, the image processor 114, the spectral processor 116, the velocity processor 118, the flow parameter processor 120 or the rendering engine 124 can be implemented via one or more processors executing one or more computer readable instructions encoded or embedded on computer readable storage medium such as physical memory or other non-transitory medium. Additionally or alternatively, at least one of the instructions can be carried by a carrier wave, a signal, or other transitory medium.

As discussed herein, the flow parameter processor 120 can determine various flow based information. A non-limiting example of this is discussed next in connection with a tubular structure or object such as a blood vessel. With this example, a flow measurement direction (i.e., an orientation of the blood vessel of interest) is known. The orientation of the blood vessel can be set manually by the end-user or, derived automatically from a B mode image or by averaging the VFI flow information over one or more heart cycles, and/or otherwise.

Given the flow measurement direction (i.e., a unit-vector pointing along the blood vessel), for each scanline within a predetermined region of interest and for all non-zero vector velocity samples, a signed projected axial mean velocity ($v_{mean}^i(m)$) can be determined based on EQUATION 1:

$$v_{mean}^j(m) = \frac{1}{N} \sum_{n=0}^{n=N-1} v^i(m,n) \cdot \bar{e}, \qquad \text{EQUATION 1}$$

where m represents a scanline number, n represents a sample number, i represents a frame number, $\bar{e}$ represents a flow measurement direction unit-vector, and N represents a number of samples per scanline and can be determined as $$N = \sum_{n=0}^{n=N-1} v^i(m,n) \cdot \bar{e} > 0.$$

In EQUATION 1, the signed axial mean velocity is signed and calculated as an average of the projection of the axial mean velocity vector into the measurement-direction vector.

A signed axial maximum velocity ($v_{max}^i(m)$) can be determined as a maximum of the projection of the axial velocity vector of each scanline within a region of interest and for all samples per scanline into the measurement direction vector, as shown in EQUATION 2:

$$v_{max}^i(m) = (\text{MAX}_{n=0}^{n=N-1} |\bar{v}^i(m,n) \cdot \bar{e}|) \text{sign}(\bar{v}^i(m,n_{max}) \cdot \bar{e}), \quad \text{EQUATION 2}$$

where $n_{max}$: $v^i(m,n_{max}) \cdot \bar{e} = \text{MAX}_{n=0}^{n=N-1} |\bar{v}^i(m,n) \cdot \bar{e}|$. This provides an estimate of the signed maximum velocity within the vessel intersected by this scanline at the time of acquisition.

A signed mean velocity ($v_{mean}(i)$) can be determined as a transverse average of the projection of the axial mean velocity vector of each scanline into the measurement direction vector, as shown in EQUATION 3:

$$v_{mean}(i) = \frac{1}{M} \sum_{m=0}^{M-1} v_{mean}^j(m). \qquad \text{EQUATION 3}$$

Unlike EQUATION 1, the signed mean velocity of EQUATION 3 averages over all of the scanlines within a region of interest, and hence over the entire acquisition-time spanned by a region of interest. In one instance, this provides for an improved quality of the mean velocity estimate relative to EQUATION 1.

Figure 4:
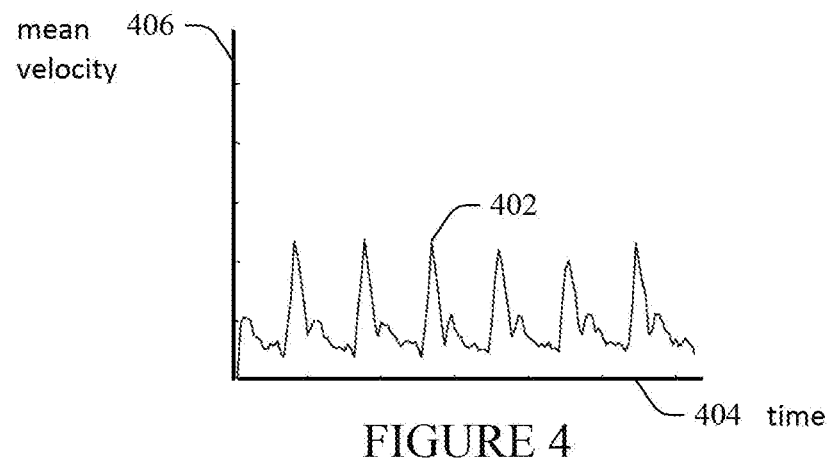
FIG. 4 illustrates an example graphical plot of a signed mean velocity flow parameter versus time.

FIG. 4 illustrates an example plot of a signed mean velocity curve trace 402 in which an x-axis 404 represents time (e.g., in units of seconds) and a y-axis 406 represents mean velocity (e.g., in units of centimeter per second, or cm/s).

A signed maximum velocity can be determined as a transverse average of the signed axial maximum, as shown in EQUATION 4:

$$v_{max}(i) = \frac{1}{M}\sum_{m=0}^{M-1} v_{max}^{i}(m). \qquad \text{EQUATION 4}$$

Unlike EQUATION 2, the signed maximum velocity of EQUATION 4 averages over all of the scanlines within a region of interest, and hence over the entire acquisition-time spanned by a region of interest. In one instance, this provides for an improved quality of the maximum velocity estimate relative to EQUATION 2.

Figure 5:
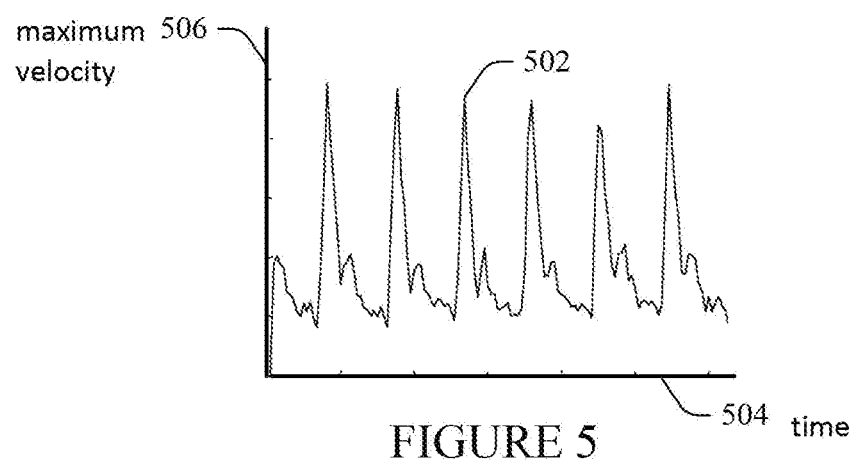
FIG. 5 illustrates an example graphical plot of a signed maximum velocity flow parameter versus time.

FIG. 5 illustrates an example plot of a signed maximum velocity curve trace 502 in which an x-axis 504 represents time (e.g., in units of seconds) and a y-axis 506 represents maximum velocity (e.g., in units of centimeter per second, or cm/s).

A signed mean volume flow (q(i)) within a blood vessel at a time of acquisition can be determined as a product of the mean velocity and a cross-section area (A) of the blood vessel (which has or approximately has longitudinal rotation symmetry), as shown in EQUATION 5:

$$q(i) = Av_{mean}(i), \qquad \text{EQUATION 5}$$

where A represents a cross-sectional area (e.g., $\pi r^2$) of the blood vessel.

Figure 6:
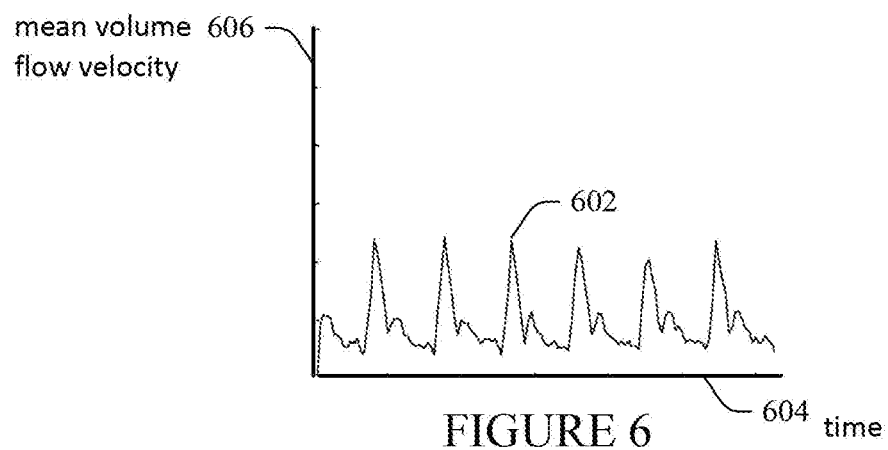
FIG. 6 illustrates an example graphical plot of a signed mean volume flow parameter versus time.

FIG. 6 illustrates an example plot of a signed mean volume flow curve trace 602 in which an x-axis 604 represents time (e.g., in units of seconds) and a y-axis 606 represents mean volume flow velocity (e.g., in units of milliliters per second, or ml/s).

A signed time average mean volume flow ($q_{TA}(i)$) over one heart cycle can be determined as shown in EQUATION 6:

$$q_{TA}(i) = \frac{1}{I}\sum_{k=0}^{I-1} q(i-k), \qquad \text{EQUATION 6}$$

where I represents the number of frames per average heart-cycle and the summation variable k represents a frame within the heart cycle.

Figure 7:
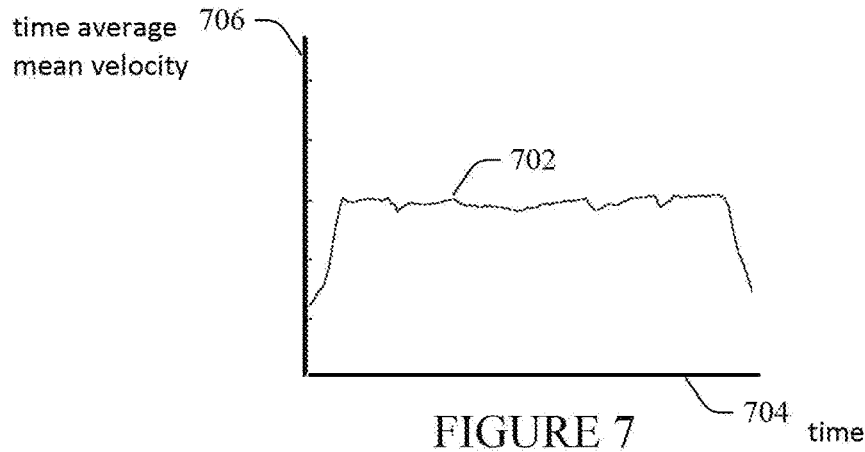
FIG. 7 illustrates an example graphical plot of a signed time average mean volume flow parameter versus time.

FIG. 7 illustrates an example plot of a signed time average mean volume flow trace 702 in which an x-axis 704 represents time (e.g., in units of seconds) and a y-axis 706 represents time average mean velocity (e.g., in units of milliliter per minute, or ml/min.

A signed stroke volume (Q(i)) can be determined as shown in EQUATION 7:

$$Q(i) = \frac{1}{FR}\sum_{k=0}^{I-1} q(i-k), \qquad \text{EQUATION 7}$$

where FR represents a frame rate.

Figure 8:
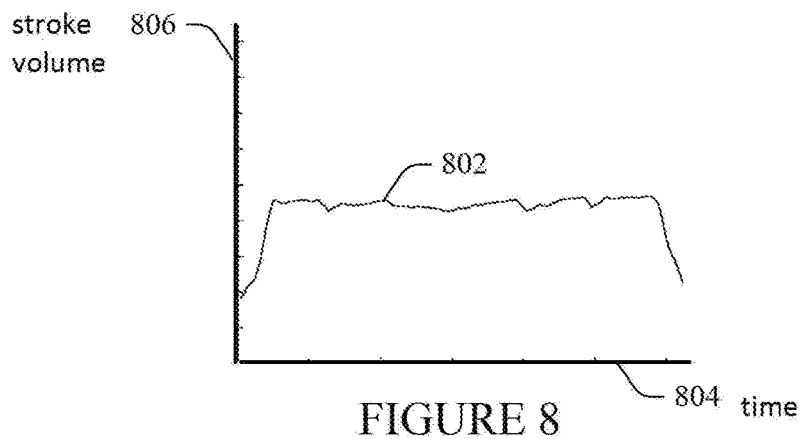
FIG. 8 illustrates an example graphical plot of a signed stroke volume parameter versus time.

FIG. 8 illustrates an example plot of a signed stroke volume trace 802 in which an x-axis 804 represents time (e.g., in units of seconds) and a y-axis 806 represents stroke volume (e.g., in units of milliliters, or ml).

Other approaches for determining flow related information are also contemplated herein. For example, another non-limiting approach for determining volume flow estimation from vector velocity images is discussed in Hansen et. al., "In Vivo Validation of a Blood Vector Velocity Estimator with MR Angiography," IEEE Transactions on UFFC Vol. 56, No. 1, January 2009. Still other approaches are also contemplated herein.

EQUATIONS 1-7 generate signed data (magnitude and direction). In a variation, at least one of the EQUATIONS 1-7 generate unsigned data (just magnitude)

Figure 9:
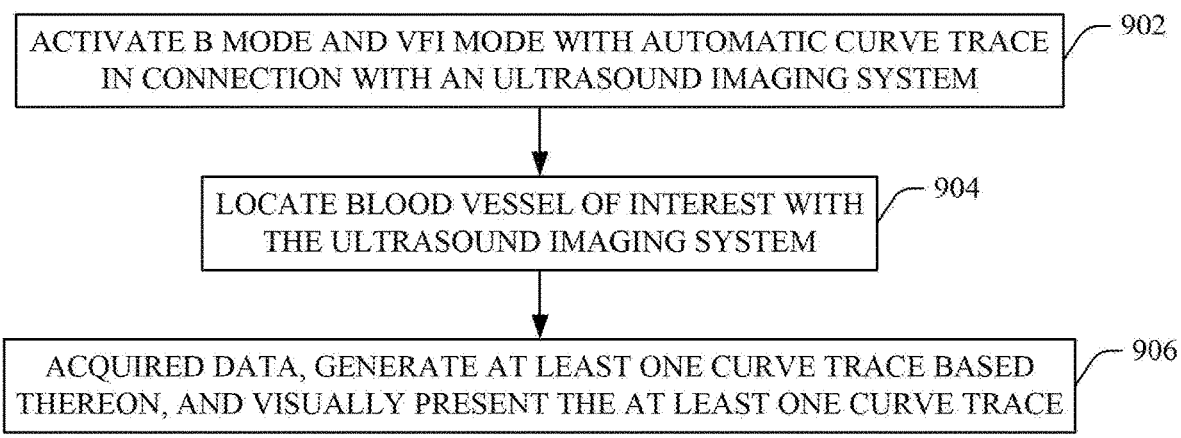
FIG. 9 illustrates an example method for determining vector flow imaging information and flow parameters therefrom.

FIG. 9 illustrates an example method.

It is to be understood that the following acts are provided for explanatory purposes and are not limiting. As such, one or more of the acts may be omitted, one or more acts may be added, one or more acts may occur in a different order (including simultaneously with another act), etc.

At 902, B-mode and VFI-mode imaging with automatic curve trace is activated for the ultrasound system 100. This can be achieved by a user through the user interface 128 and/or otherwise.

At 904, the transducer 102 of the ultrasound imaging system 100 is employed to scan a subject and locate a blood vessel of interest for evaluation. This can be achieved by a user moving the transducer 102 over a region of the subject which includes the vessel.

At 906, in response to locating the vessel, the transducer 102 is used to acquire data over a predetermined time duration (e.g., at least two heart beats), and the flow parameter processor 120 and the rendering engine 124 system 100, respectively, determines and visually presents at least one flow parameter via the display 126.

As described herein, this may include, concurrently with act 906, visually displaying a B mode image with vector flow imaging information superimposed there over along with the at least one flow parameter.

The methods described herein may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound system, comprising:
    a display;
    a velocity processor that processes ultrasound data representing structure flowing through a tubular object and generates vector flow imaging information indicative of the structure flowing through the tubular object based on the processed ultrasound data,
    wherein the vector flow imaging information includes an axial velocity component signal and a lateral component signal, and the axial velocity and the lateral component signals indicate a direction and a speed of the structure flowing through the tubular object;

a flow parameter processor that determines at least one signed flow parameter based on the vector flow imaging information and a flow parameter algorithm from a set of algorithms, wherein the at least one signed flow parameter includes both a magnitude and the direction of the structure flowing through the tubular object and includes a signed projected axial mean velocity, and generates a signal indicative of the at least one signed flow parameter, wherein the signed projected axial mean velocity is determined from $$\frac{1}{N}\sum_{n=0}^{n=N-1} v^i(m,n)\cdot \bar{e},$$

where m represents a scanline number, n represents a sample number, i represents a frame number, $\bar{e}$ represents a flow measurement direction unit-vector, and N represents a number of samples per scanline;

an image processor that processes the ultrasound data representing the structure flowing through the tubular object and generates at least one image based on the processed ultrasound data; and a rendering processor that concurrently visually displays, via the display, the at least one image, the vector flow imaging information, and the at least one signed flow parameter representing a projection into a measurement direction vector as a graphical plot versus time and indicating the direction of the structure flowing through the tubular object.

2. The system of claim 1, wherein the at least one signed flow parameter further includes one or more of a velocity variance, a velocity standard deviation, a peak systolic velocity, or an end diastolic velocity.

3. The system of claim 1, wherein the rendering processor visually displays the at least one signed flow parameter as a numerical value.

4. The system of claim 1, wherein the velocity processor processes the ultrasound data as the ultrasound data is produced, the flow parameter processor processes the velocity flow imaging information as the velocity flow imaging information is produced, and the rendering processor visually displays the velocity flow imaging information and the at least one signed flow parameter as the velocity flow imaging information and the at least one signed flow parameter are produced.

5. The system of claim 4, further comprising:
a transducer array that receives a set of echoes generated in response to the structure flowing through the tubular object; and
processing circuitry that processes the set of echoes as the set of echoes are received, generating the ultrasound data.

6. The system of claim 1, wherein the at least one signed flow parameter is visually displayed as at least one of a velocity or a volume flow profile curve as a function of time versus at least one of an axial or a lateral distance through the tubular structure.

7. The system of claim 1, wherein the at least one signed flow parameter is visually displayed as at least one of a velocity or a volume flow profile curve as a function of time versus a spatial line through the tubular object.

8. The system of claim 1, wherein the at least one signed flow parameter indicates a cross-section area of the tubular object.

9. The system of claim 1, wherein the at least one signed flow parameter is determined for a predetermined region of interest, which is a sub-region of the tubular object.

10. The system of claim 1, wherein the flow parameter processor further determines a signed mean velocity as a transverse average of the projection of the axial mean velocity vector of each scanline into the measurement direction vector.

11. A method, comprising:
processing ultrasound data representing structure flowing through a tubular object and generating vector flow imaging information indicative of the structure flowing through the tubular object based on the processed ultrasound data, wherein the vector flow imaging information includes an axial velocity component signal and a lateral component signal, and the axial velocity and the lateral component signals indicate a direction and a speed of the structure flowing through the tubular object;

determining at least one signed flow parameter based on the vector flow imaging information and a flow parameter algorithm from a set of algorithms, wherein the at least one signed flow parameter includes both a magnitude and the direction of the structure flowing through the tubular object and includes a signed axial maximum velocity, and a signed stroke volume, and generating a signal indicative of the at least one signed flow parameter, wherein the signed axial maximum velocity is determined from $(\text{MAX}_{n=0}^{n=N-1}|\bar{v}^i(m,n)\cdot\bar{e}|)\text{sign}(\bar{v}^i(m,n_{max})\cdot\bar{e})$, where m represents a scanline number, n represents a sample number, i represents a frame number, $\bar{e}$ represents a flow measurement direction unit-vector, and N represents a number of samples per scanline;

processing the ultrasound data representing the structure flowing through the tubular object and generating at least one image based on the processed ultrasound data; and concurrently visually displaying the at least one image, the vector flow imaging information, and the at least one signed flow parameter representing a projection into a measurement direction vector as a graphical plot versus time and indicating the direction of flow within the tubular object.

12. The method of claim 11, wherein the at least one signed flow parameter further includes one or more of a velocity variance, a velocity standard deviation, a peak systolic velocity, or an end diastolic velocity.

13. The method of claim 11, further comprising: visually displaying the at least one signed flow parameter as at least one of a numerical value.

14. The method of claim 13, further comprising:
updating the at least one of the numerical value or the graphical plot as the vector flow imaging information is generated.

15. The method of claim 11, further comprising: visually displaying the at least one signed flow parameter as at least one of a velocity or a volume flow profile curve as a function of time versus at least one of an axial or a lateral distance through the tubular structure.

16. The method of claim 11, further comprising: visually displaying the at least one signed flow parameter as at least one of a velocity or a volume flow profile curve as a function of time versus at least one of a spatial line through the tubular structure.

17. The method of claim 11, wherein the at least one signed flow parameter indicates a cross-section area of the tubular structure.

18. The method of claim 11, wherein the at least one signed flow parameter is determined for a predetermined region of interest, which is a sub-region of the tubular structure.

19. The method of claim 11, wherein the determination of the at least one signed flow parameter comprises determining a signed maximum velocity determined as a transverse average of the signed axial maximum.

20. A non-transitory computer readable storage medium encoded with computer readable instructions, which, when executed by a processor, causes the processor to:
    process ultrasound data representing structure flowing through a tubular object and generate vector flow imaging information indicative of the structure flowing through the tubular object based on the processed ultrasound data,
    wherein the vector flow imaging information includes an axial velocity component signal and a lateral component signal, and the axial velocity and the lateral component signals indicate a direction and a speed of the structure flowing through the tubular object;
    determine at least one signed flow parameter based on the vector flow imaging information and a flow parameter algorithm from a set of algorithms, wherein the at least one signed flow parameter includes both a magnitude and the direction of the structure flowing through the tubular object and is selected from a group consisting of a signed time average mean volume flow and a signed stroke volume, and generate a signal indicative of the at least one signed flow parameter;
    process the ultrasound data representing the structure flowing through the tubular object and generate at least one image based on the processed ultrasound data; and
    concurrently visually display the at least one image, the vector flow imaging information, and the at least one signed flow parameter representing a projection into a measurement direction vector as a graphical plot versus time and indicating the direction of flow within the tubular object,
    wherein the signed time average mean volume flow is determined from $Av_{mean}(i)$, where A represents a cross-sectional area of a blood vessel and i represents a frame number, or
    $$\frac{1}{I}\sum_{k=0}^{I-1} q(i-k),$$
    where i represents a frame number, I represents a number of frames per average heart-cycle, and a summation variable k represents a frame within a heart cycle, and
    wherein the signed stroke volume (Q(i)) is determined from
    $$\frac{1}{FR}\sum_{k=0}^{I-1} q(i-k),$$
    where FR represents a frame rate.

21. The non-transitory computer readable storage medium of claim 20, wherein the computer readable instructions further cause the processor to: visually display the at least one signed flow parameter as a numerical value.

22. The non-transitory computer readable storage medium of claim 21, wherein the computer readable instructions further cause the processor to:
    update the at least one of the numerical value or the graphical plot as the vector flow imaging information is generated.

23. The non-transitory computer readable storage medium of claim 20, wherein the computer readable instructions further cause the processor to: visually display the at least signed one flow parameter as at least one of a velocity or a volume flow profile curve as a function of time versus at least one of an axial or a lateral distance through the tubular structure.

24. The non-transitory computer readable storage medium of claim 20, wherein the computer readable instructions further cause the processor to: visually display the at least one signed flow parameter as at least one of a velocity or a volume flow profile curve as a function of time versus at least one of a spatial line through the tubular structure.

* * * * *